United States Patent [19]

Kuwahara et al.

[11] Patent Number: 5,081,024

[45] Date of Patent: Jan. 14, 1992

[54] PROCESS FOR PRODUCING OPTICALLY ACTIVE AMINO ACIDS

[75] Inventors: Masao Kuwahara, Funabashi; Michito Tagawa, Omiya; Takashi Furusato, Yono; Hiroyuki Narushima, Kuki; Shuzo Shinke, Funabashi, all of Japan

[73] Assignee: Nissan Chemical Industries, Ltd., Tokyo, Japan

[21] Appl. No.: 396,694

[22] Filed: Aug. 22, 1989

[30] Foreign Application Priority Data

| Sep. 5, 1988 | [JP] | Japan | 63-221899 |
|---|---|---|---|
| Dec. 23, 1988 | [JP] | Japan | 63-325125 |
| Jan. 19, 1989 | [JP] | Japan | 1-10826 |
| Jan. 20, 1989 | [JP] | Japan | 1-11636 |
| Mar. 14, 1989 | [JP] | Japan | 1-61711 |
| Apr. 28, 1989 | [JP] | Japan | 1-110281 |
| Jun. 7, 1989 | [JP] | Japan | 1-144437 |
| Jul. 14, 1989 | [JP] | Japan | 1-181823 |

[51] Int. Cl.$^5$ .................. C12P 13/04; C12P 13/20; C12P 13/14; C12N 9/78

[52] U.S. Cl. .................. 435/106; 435/109; 435/110; 435/280; 435/227; 435/228; 435/252.1; 435/252.5; 435/833; 435/850; 435/829; 435/824; 435/883; 435/827; 435/907; 435/881

[58] Field of Search ............... 435/227, 228, 229, 280, 435/106, 109, 110

[56] References Cited

U.S. PATENT DOCUMENTS

| 3,816,254 | 6/1974 | Chibata | 195/29 |
|---|---|---|---|
| 3,963,573 | 6/1976 | Stauffer | 195/29 |
| 4,226,941 | 10/1980 | Goi et al. | |
| 4,389,488 | 6/1983 | Grabley et al. | |

FOREIGN PATENT DOCUMENTS 60-62991 4/1985 Japan.
62-44181 2/1987 Japan.

OTHER PUBLICATIONS

*Bergey's Manual of Determinative Bacteriology*, Eighth Edition, 1974, pp. 326-327, 483 and 707.
*Bergey's Manual of Determinative Bacteriology*, Eighth Edition, 1984, pp. 356, 363-365.
Chemical Abstracts, vol. 90, No. 13, 3/26/79, pp. 436-437, Abstract No. 10196c, Yakuhin.

*Primary Examiner*—Douglas W. Robinson
*Assistant Examiner*—C. Geckle
*Attorney, Agent, or Firm*—Nixon & Vanderhye

[57] ABSTRACT

An efficient process of optical resolution is provided for producing an L-amino acid represented by the following formula (I):

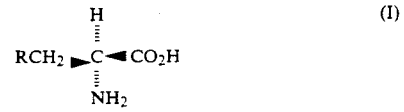

wherein R is $-CH_2CO_2H$, $-CH_2CONH_2$, $-CO_2H$ or

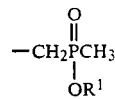

in which $R^1$ is hydrogen atom, an alkyl group having 1 to 10 carbon atoms or a halogen-substituted alkyl group having 1 to 10 carbon atoms. The process comprises an optical resolution of an N-substituted carbonyl-D,L-amino acid represented by the formula (II):

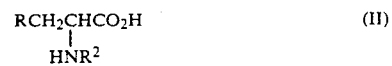

(wherein R is the same as defined above and $R^2$ is an alkanoyl group having 1 to 5 carbon atoms, benzoyl group, a halogen-substituted alkanoyl group having 1 to 5 carbon atoms or a halogen-substituted benzoyl group), its salt or a mixture thereof, by means of cells of a microorganism, a fermentation broth of a microorganism, a treated fermentation broth of a microorganism or a mixture thereof, said microorganism being selected from the bacteria of the genera Serratia, Staphylococcus, Bacillus, Flavobacterium, Achromobacter and Alcaligenes and actinomycetes of the genera Actinoplanes, Streptosporangium and Sebekia.

14 Claims, 3 Drawing Sheets

PROCESS FOR PRODUCING OPTICALLY ACTIVE AMINO ACIDS

FIELD OF THE INVENTION

The present invention relates to a process for the enzymatic optical resolution of an N-substituted carbonyl-D,L-amino acid and/or salt thereof, which can be obtained by an inexpensive chemical synthesis, into corresponding an L-amino acid and an N-substituted carbonyl-D-amino acid by means of cells of a microorganism, a fermentation broth of a microorganism, and/or a treated fermentation broth of a microorganism.

BACKGROUND OF THE INVENTION

Methods for producing L-amino acids from N-acyl-D,L-amino acids have been known in the art (see, for example, Japanese Patent Application Laid-Open (Kokai) No. 22188/88).

However, the deacyl enzymes reported previously show a weak activity in deacylating N-acylated compounds of phosphorus-containing amino acids or acidic amino acids.

L-2-amino-4-hydroxy(methyl)phosphinylbutyric acid represented by the formula (III):

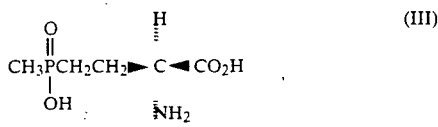

which is one target compound of the invention, is a compound useful as a herbicide named Glufosinate (common name). Racemic 2-amino-4-hydroxy(methyl)-phosphinylbutyric acid is currently used for the purpose. Actually, only the L-isomer shows the herbicidal activity. Thus, it has been desired to develop a method capable of producing potent L-2-amino-4-hydroxy(methyl)phosphinylbutyric acid selectively and inexpensively.

In recent years, there have been required those agricultural chemicals which are not only highly potent as pesticides but also mild to the environment. For decreasing the influence upon the environment, it is desirable not to release inactive isomers into the environment at use of the agricultural chemicals.

A fermentation method is known to produce L-2-amino-4-hydroxy(methyl)phosphinylbutyric acid, but is expensive.

As for enzymatic production of L-2-amino-4-hydroxy-(methyl)phosphinylbutyric acid from N-acyl-D,L-2-amino-4-hydroxy(methyl)phosphinylbutyric acid, there have been reported to date only the following two methods, a method using cells of microorganisms belonging to the genus Pseudomonas, Streptomyces or Aspergillus (Japanese Patent Application Laid-Open No. 47630/80) and a method using penicillin G-acylase (Japanese Patent Application Laid-Open Nos. 138394/82 and 51099/89).

However, L-2-amino-4-hydroxy(methyl)phosphinylbutyric acid obtained by the former method shows an optical rotation of 23° (C=1, 1N HCl) at the maximum, the optical purity being low (ca. 75%) (Japanese Patent Application Laid-Open No. 51099/89). Also, the working temperature of the enzymes is in the range of 28° to 35° C. and the inactivation occurs at 50° C. (Japanese Patent Application Laid-Open No. 47630/80). Thus, the method is not practical for industrial production. In addition, they show only a weak action or no action at all on the acylated compounds of L-amino acids other than N-acyl-L-2-amino-4-hydroxy(methyl)-phosphinyl-butyric acids (Japanese Patent Application Laid-Open No. 47630/80).

It is also known that conventional aminoacylase is quite inactive to the acyl group of N-acyl-D,L-2-amino-4-hydroxy(methyl)phosphinylbutyric acids (Japanese Patent Application Laid-Open No. 138394/82).

On the other hand, the latter method using penicillin G-acylase is not practical because a phenacyl group is used as an eliminating group.

SUMMARY OF THE INVENTION

As a result of intensive studies for solving said problems of the prior art, the present inventors have succeeded in finding out microorganisms which are capable of converting only the L-isomers of N-substituted carbonyl-D,L-amino acids into corresponding L-amino acids by stereo-selective elimination of the substituted carbonyl group (e.g., deacetylation) of the L-isomer alone, and thus have achieved the present invention.

The present invention relates to a process for producing an L-amino acid represented by the formula (I):

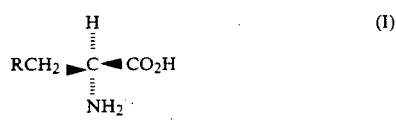

(wherein R is —CH$_2$CO$_2$H, —CH$_2$CONH$_2$, —CO$_2$H or

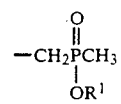

in which R$^1$ is hydrogen atom, an alkyl group having 1 to 10 carbon atoms or a halogen-substituted alkyl group having 1 to 10 carbon atoms), which process comprising carrying out an optical resolution of an N-substituted carbonyl-D,L-amino acid represented by the formula (II):

(wherein R is the same as defined above and R$^2$ is an alkanoyl group having 1 to 5 carbon atoms, benzoyl group, a halogen-substituted alkanoyl group having 1 to 5 carbon atoms or a halogen-substituted benzoyl group), its salt or a mixture thereof, which can be produced inexpensively by amidocarbonylation or other methods, by means of cells of a microorganism, a fermentation broth of a microorganism, and/or treated fermentation broth of a microorganism, said microorganism being selected from the bacteria belonging to the genera Serratia, Staphylococcus, Bacillus, Flavobacterium, Achromobacter and Alcaligenes, and the actinomycetes belonging to the genera Actinoplanes, Streptosporangium and Sebekia.

DETAILED DESCRIPTION OF THE PREFERRED EMBODIMENTS

Figure 1:
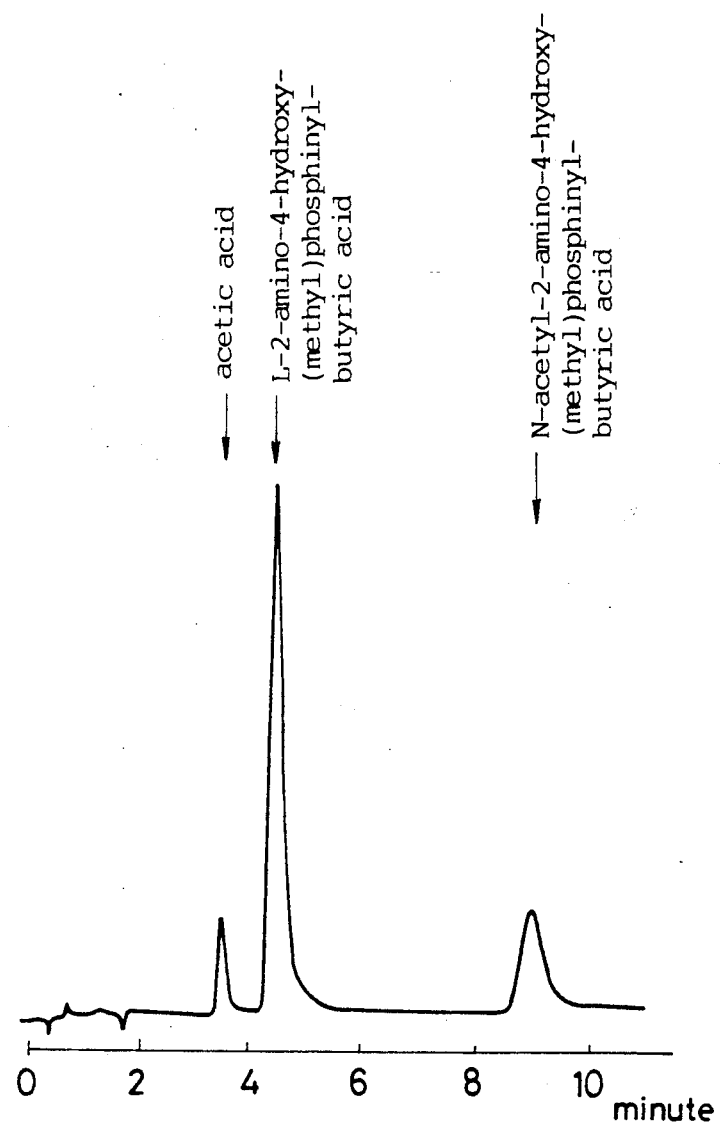

In the N-substituted carbonyl-D,L-amino acids and/or salts thereof represented by the formula (II), examples of the substituent $R^1$ of an alkyl group having 1 to 10 carbon atoms include methyl, ethyl, n-propyl, i-propyl, n-butyl, i-butyl, t-butyl, pentyl, hexyl, heptyl, octyl, nonyl, and decyl groups.

Halogen atom in the substituent $R^1$ of a halogen-substituted alkyl having 1 to 10 carbon atoms may be, for example, chlorine atom or bromine atom. Examples of the alkyl group include chloroethyl, chloropropyl, chlorobutyl, chloropentyl, chlorohexyl, chloroheptyl, chlorooctyl, chlorononyl, chlorodecyl, bromoethyl, bromopropyl, bromobutyl, bromopentyl, bromohexyl, bromoheptyl, bromooctyl, bromononyl, and bromodecyl groups.

The substituted carbonyl group $R^2$ of an alkanoyl group having 1 to 5 carbon atoms may be formyl, acetyl, propionyl, n-butyryl, i-butyryl, n-pentanoyl, or i-pentanoyl group and the like.

The substituted carbonyl group $R^2$ may also represent a halogen-substituted alkanoyl group having 1 to 5 carbon atoms, in which halogen atom may be chlorine atom or bromine atom, for example. Example of the alkanoyl group include chloroacetyl, chloropropionyl, chlorobutyryl, chloropentanoyl, bromocarbonyl, bromoacetyl, bromopropionyl, bromobutyryl, and bromopentanoyl groups.

The substituted carbonyl group $R^2$ can further be a halogen-substituted benzoyl group, in which chlorine atom and bromine atom are illustrative as the halogen atom. Typical examples of the halogen-substituted benzoyl groups are chlorobenzoyl and bromobenzoyl groups.

Furthermore, the substituted carbonyl group $R^2$ may be any of substituted carbonyl groups provided that they can be eliminated by a microbial enzyme according to the present invention to form a corresponding L-amino acid.

The salts of N-substituted carbonyl-D,L-amino acids of the formula (II), which can be used in the invention as starting material, may be sodium salts, potassium salts, ammonium salts or calcium salts, for example.

The microorganisms according to the present invention are those selected from the bacteria belonging to the genera Serratia, Staphylococcus, Bacillus, Flavobacterium, Achromobacter and Alcaligenes and the actinomycetes belonging to the genera Actinoplanes, Streptosporangium and Sebekia, and are capable of stereo-selective elimination of the substituted carbonyl group (e.g., deacylation) of only the L-isomer of an N-substituted carbonyl-D,L-amino acid and/or salt thereof used as starting material in this invention.

These microorganisms can be selected from the stock strains which are usually easy to obtain or purchase. They can be also collected or separated from the natural sources.

It is possible to produce their variants having higher productivity by mutation of the above microorganisms.

It is also possible to artificially prepare an enzyme-producing strain of the present invention by cutting out a gene relating to the enzyme production present in the cells of the above-mentioned strains, inserting such gene into an appropriate vector such as plasmid, and transforming a suitable heterologous or homologous host such as *Escherichia coli*, *Bacillus subtilis* or actinomycetes by using the resulting vector.

Among the microorganisms usable in this invention, *Serratia marcescens* IFO 12648, *Staphylococcus aureus* IFO 12732 and *Achromobacter* sp. IFO 13495 can be mentioned as the examples of easily available bacteria.

*Actinoplanes liguriae* IFO 13997 and *Sebekia benihana* IFO 14309 are the examples of easily available actinomycetes.

As examples of the bacteria separated from soil by the present inventors, there can be mentioned *Bacillus brevis* NCB 11 and *Flavobacterium* sp. NCB 12-2, which were separated from the soil in Shiraoka, Saitama, and *Alcaligenes latus* NCB 4-12 separated from the soil in Itoh, Shizuoka.

*Streptosporangium* sp. NC 26 separated from the soil in Saitama is an example of actinomycetes separated from soil.

The mycological characteristics of these microorganisms are as follows:

1. Mycological characteristics of Bacillus brevis NCB 11
   A. Morphological characteristics
      (1) Shape and size: rods;
         0.6–0.9 μm in diameter;
         2.0–4.0 μm in length
      (2) Polymorphism: singly or in pairs
      (3) Motility: positive
      (4) Spore formation: positive; Spore shape: ellipsoidal; Spore position: subterminal; Sporangium: slightly swollen;
      (5) Gram-stain: positive
   B. Growth characteristics
      (1) Growth on nutrient agar moderate growth, lustrous surface, opaque and creamy white.
      (2) Growth on nutrient agar slant moderate and homogeneous growth, lustrous surface, opaque and creamy white
      (3) Growth in nutrient broth moderate growth, growth on surface with pellicle, slightly turbid with the progress of cultivation, creamy white.
      (4) Growth in litmus milk peptonized with a slight degree of litmus decoloration.
      (5) Growth in nutrient gelatin stab liquefied.
   C. Physiological characteristics
      (1) Nitrite from nitrate: positive
      (2) Denitrification: negative
      (3) Methyl red test: negative
      (4) Voges-Proskauer reaction: negative, pH of the broth = 7.8
      (5) Indole formation: negative
      (6) $H_2S$ formation: negative
      (7) Hydrolysis of starch: negative
      (8) Citrate utilization: positive
      (9) Egg-yolk lecithinase: negative
      (10) Pigment formation: negative
      (11) Catalase: positive
      (12) Hydrolysis of gelatin: positive
      (13) pH for growth: able to grow at pH 6–9; unable to grow at pH 5.7
      (14) Temperature for growth: able to grow at 15–50° C. unable to grow at 10° C. or 55° C.
      (15) Oxygen requirement: aerobic growth
      (16) NaCl tolerance: unable to grow at 5%
      (17) Degradation of tyrosine: positive
   D. Acid formation from carbohydrates
      L-arabinose : —
      D-xylose : —

D-glucose : +
D-mannitol : +

By comparing the mycological properties of NCB 11 strain with the descriptions in Bergey's Manual of Systematic Bacteriology, NCB 11 strain can be regarded as a strain belonging to the species *Bacillus brevis* in view of the morphological, growth and physiological characteristics as well as acid formation from carbohydrates. This strain is deposited at Fermentation Research Institute, Tsukuba, Ibaragi in Japan, with accession number FERM P-10457 (date of deposit; December 20, 1988), which were then converted on Aug. 14, 1989 to accession number FERM BP-2551 under the Budapest Treaty on the International Recognition of the Deposit of Microorganisms for the Purpose of Patent Procedure.

2. Mycological characteristics of Flavobacterium sp. NCB 12-2.
   A. Morphological characteristics
      (1) Shape and size: rods;
         0.4-0.6 μm in diameter;
         1.0-2.0 μm in length
      (2) Polymorphism: singly or in pairs
      (3) Motility: negative
      (4) Spore formation: negative
      (5) Gram-stain: negative
   B. Growth characteristics
      (1) Growth on nutrient agar moderate and homogeneous growth, opaque and yellow
      (2) Growth on nutrient agar slant moderate and homogeneous growth, opaque and yellow
      (3) Growth in nutrient broth moderate growth, growth on surface, slightly turbid with the progress of cultivation, creamy white
      (4) Growth in litmus milk quickly peptonized with a slight degree of litmus decoloration.
      (5) Growth in nutrient gelatin stab liquefied.
      (6) Growth on Simmons' citrate agar slant unable to grow
      (7) Growth on Cetrimide agar slant unable to grow
   C. Physiological characteristics
      (1) Nitrite from nitrate: negative
      (2) Denitrification: negative
      (3) Methyl red test: negative
      (4) Voges-Proskauer reaction: negative
      (5) Indole formation: positive
      (6) $H_2S$ formation: negative
      (7) Hydrolysis of starch: positive
      (8) Degradation of casein: positive
      (9) Hydrolysis of esculin: positive
      (10) Pigment formation: water-insoluble yellow pigment
      (11) Oxidase: positive
      (12) Catalase: positive
      (13) Hydrolysis of gelatin: positive
      (14) pH for growth: able to grow at pH 5-9
      (15) Temperature for growth: able to grow at 15°-45° C., optimum temperature: 25°-35° C.
      (16) Oxygen requirement: aerobic growth
      (17) O-F test: Acid is produced oxidatively from glucose but no gas is produced.
      (18) Degradation of urea: positive
   D. Acid formation from carbohydrates
      L-arabinose: $-^{1)}$
      ethanol : $-^{1)}$
      D-xylose : $-^{1)}$
      D-glucose : $-^{1)}$
      salicin : $-^{1)}$
      sucrose : $-^{1)}$
      cellobiose : $-^{1)}$
      D-mannitol : $-^{1)}$
      lactose : $-^{1)}$
      raffinose : $-^{1)}$
      adonitol : $-^{2)}$
      D-xylose : $-^{2)}$
      D-glucose : $+^{2)}$
      sucrose : $-^{2)}$
      maltose : $+^{2)}$
      lactose : $-^{2)}$ 1) tested in an ammonium salt medium
2) tested in OF medium By comparing the mycological properties of NCB 12-2 strain with the descriptions in Bergey's Manual of Systematic Bacteriology, NCB 12-2 strain can be regarded as a strain belonging to the genus Flavobacterium and analogous to *Flavobacterium meningosepticum* in view of the morphological, growth and physiological characteristics as well as acid formation from carbohydrates. This strain is deposited at Fermentation Research Institute, Tsukuba, Ibaragi in Japan, with accession number FERM P-10459 (date of deposit; Dec. 20, 1988), which were then converted on Aug. 14, 1989 to accession number FERM BP-2552 under the Budapest Treaty on the International Recognition of the Deposit of Microorganisms for the Purpose of Patent Procedure.

3. Mycological characteristics of Alcaligenes latus NCB 4-12
   A. Morphological characteristics
      (1) Shape and size: rods;
         1.0-1.5 μm in diameter;
         1.5-3.0 μm in length
      (2) Polymorphism: singly or in pairs
      (3) Motility: motile with peritrichous flagella
      (4) Spore: negative
      (5) Gram-stain: negative
   B. Growth characteristics
      (1) Growth on nutrient agar moderate growth, white or pale yellow, wrinkled with progress of cultivation
      (2) Growth on nutrient agar slant moderate and homogeneous growth, translucent and white or pale yellow
      (3) Growth in nutrient broth moderate growth, becomes turbid with progress of cultivation, creamy white
      (4) Growth in litmus milk not liquefied
      (5) Growth in nutrient gelatin stab liquefied
   C. Physiological characteristics
      (1) Nitrite from nitrate: positive
      (2) Reduction of nitrite: negative
      (3) Anaerobic growth with nitrate: unable to growth
      (4) Anaerobic growth with nitrite: unable to growth
      (5) Oxidase: positive
      (6) Catalase: positive
      (7) Hydrolysis of starch: positive
      (8) Hydrolysis of Tween 80: positive
      (9) Hydrolysis of urea: negative
      (10) 3-Ketolactose formation: negative
      (11) Acid from D-glucose or D-xylose in O-F medium: negative
      (12) pH for growth: able to grow at pH 5-9
      (13) Temperature for growth: able to grow at 15°-45° C.

D. Carbon source for growth
   L-arabinose : −
   D-xylose : −
   D-glucose : +
   D-mannitol : −
   maltose : +
   D-mannose : −
   D-fructose : −
   adipate : −

By comparing the mycological properties of NCB 4-12 strain with the descriptions in Bergey's Manual of Systematic Bacteriology, NCB 4-12 strain can be regarded as a strain belonging to the species *Alcaligenes latus* in view of the morphological, growth and physiological characteristics as well as utilization of carbohydrates. This strain is deposited at Fermentation Research Institute, Tsukuba, Ibaragi in Japan, with accession number FERM P-10660 (date of deposit; April 13, 1989), which were then converted on August 14, 1989 to accession number FERM BP-2553 under the Budapest Treaty on the International Recognition of the Deposit of Microorganisms for the Purpose of Patent Procedure.

4. Mycological characteristics of Streptosporangium sp. NC 26

(1) Morphological characteristics

It forms aerial mycelium, on which spherical sporangia grow. Sporangiospores are non-motile. The substratal mycelium is branched and not separated.

(2) Composition of cell wall
2,6-Diaminopimelic acid, meso type.

(3) Carbohydrate composition of the whole cell
galactose, glucose, mannose, madurose, and ribose (4) Menaquinone
MK-9($H_2$), MK-9($H_0$), MK-9($H_4$)

(5) Growth characteristics in each medium (at 25° C. for 21 days)
  (1) Sucrose-nitrate agar
      moderate growth, white
  (2) Glucose-asparagine agar moderate growth, white or pale creamy color
  (3) Glycerol-asparagine agar
      moderate growth, white
  (4) Inorganic salts-starch agar
      poor growth, white
  (5) Tyrosine agar
      poor growth, white
  (6) Nutrient agar
      moderate growth, pale yellow
  (7) Yeast extract-malt extract agar
      good growth, pale yellow or orange
  (8) Oatmeal agar
      poor growth, white (6) Physiological characteristics
  (1) Temperature for growth: 10–45° C.,
      optimum temperature: 25–35° C.
  (2) pH for growth: 5.0–10.0
      optimal pH 7.0–8.0
  (3) Hydrolysis of gelatin: positive
  (4) hydrolysis of starch: positive
  (5) Coagulation and peptonization of skim milk: both negative
  (6) Formation of melanin-like pigment: negative (7) Carbon utilization (Pridham and Gottlieb agar)
   L-arabinose: +
   D-xylose : +
   D-glucose : +
   D-fructose : +
   sucrose : +
   inositol : +
   L-rhamnose : −
   raffinose : −
   D-mannitol : +

By comparing the mycological properties of NC 26 strain with the descriptions in Bergey's Manual of Determinative Bacteriology (8th edition), NC 26 strain can be regarded as a strain belonging to the genus Streptosporangium in view of the morphological and growth characteristics, physiological characteristics and utilization of carbohydrates. This strain is deposited at Fermentation Research Institute, Tsukuba, Ibaragi in Japan, with accession number FERM P-10752 (date of deposit; May 31, 1989), which were then converted on Aug. 14, 1989 to accession number FERM BP-2554 under the Budapest Treaty on the International Recognition of the Deposit of Microorganisms for the Purpose of Patent Procedure.

The microbial strains usable in the present invention are not limited to those mentioned above.

A microorganism used in this invention is usually cultivated under aerobic fermentation conditions, such as shaking culture or aerated stirring deep culture. Cultivation temperature ranges 20 to 37° C, and the pH is in the range of 6 to 9. Cultivation is continued for 1 to 7 days.

The culture medium used in the invention contains an assimilable carbon source, a nitrogen source, an inorganic salt and a trace amount of organic nutrient.

As the carbon source, carbohydrates such as glucose, maltose, starch hydrolyzate and glucose syrup can be used.

As the nitrogen source, there can be used ammonia and various kinds of organic and inorganic ammonium salts such as ammonium sulfate and ammonium chloride, as well as natural organic nitrogen sources such as meat extract, yeast extract, polypepton, corn steep liquor, casein hydrolyzate, and the like.

The inorganic salts may be salts of magnesium, iron, manganese, potassium, sodium, calcium, cobalt, and the like.

In order to induce or enhance the aimed enzyme production, an N-substituted carbonyl-D,L-amino acid of the formula (II), which serves as a substrate of the aimed enzyme, or a structural analogs of said substrate may be added in the early stage or in the course of cultivation within a limit not harmful to the growth of the microorganism.

Cells of a microorganism and/or a treated fermentation broth used in the present invention may be obtained from a fermentation broth produced in the manner described above and then employed in the optical resolution according to the present invention.

The term "a fermentation broth" used herein refers to a product obtained by the cultivation of the microorganism, including the cells themselves.

The term "a treated fermentation broth" used herein means a fermentation broth subjected to any of the treatments such as centrifugation, filtration, homogenation using a homogenizer, sonication, treatments with a organic solvent or other organic or inorganic substance, or combination thereof. Examples of the treated fermentation broth include a broth filtrate, a supernatant, treated cells defined hereinafter and the like.

The fermentation broth is separated into cells and a broth filtrate (supernatant) by centrifugation, for example. When a substituted carbonyl-eliminating enzyme (e.g., deacylating enzyme) exists in the cells, said cells and/or treated cells thereof are used.

The term "treated cells" used herein refer to a sonicate of the cells, a crushed product thereof using homogenizer, cells treated with an organic solvent such as acetone or toluene, or cells treated with a surface active agent such as Triton X-100.

Also, the enzyme may be separated from the fermentation broth by properly combining the known methods to prepare an enzyme sample with different degree of purity.

In case a substituted carbonyl group-eliminating enzyme such as deacyl enzyme is present outside the cells, such enzyme may be collected from the culture broth and purified.

It is also a preferred embodiment of the present invention to use the cells or a treated fermentation broth or an enzyme sample of different degree of purity in the optical resolution after immobilizing them onto a carrier by a known method.

It is possible to use any type of carriers as far as they will not cause inactivation of the enzyme at the fixing. Examples of such carrier include alginic acid, carrageenan, chitosan, polyacrylamide, and photo-crosslinkable resins.

There is no specific limitation of the concentration of the N-substituted carbonyl-D,L-amino acids of the formula (II) and/or salts thereof used as substrates in this invention, but usually such substrates are used in a concentration of 0.5 to 20%.

Reaction temperature of the optical resolution is in the range of 10° to 60° C., preferably 20° to 50° C.

The optical resolution is continued for 0.5 to 4 days while keeping pH of the reaction solution in the range of 4 to 10, preferably 6 to 9.

Known methods can be used for separating L-amino acids and N-substituted carbonyl-D-amino acids from the reaction mixture. For example, one may employ a direct crystallization involving concentration or isoelectronic point precipitation, or a treatment with ion exchange resins.

Thin-layer chromatography, high performance liquid chromatography and/or bioassay can be used for the qualitative and quantitative analyses of the L-amino acids produced.

The optical isomers can be determined by optical rotation analysis, high performance liquid chromatography using optical isomer-separating columns.

The unreacted N-substituted carbonyl-D-amino acids can be chemically racemized by a conventional method and the racemic product can be recycled to the above-mentioned optical resolution.

According to the present invention, it is possible to selectively produce the optically active L-amino acids and N-substituted carbonyl-D-amino acids from N-substituted carbonyl-D,L-amino acids, their salts, or a mixture thereof which can be easily synthesized according to a chemical process of amidocarbonylation.

The substituted carbonyl group-eliminating enzymes used in the invention effectively eliminate the substituted carbonyl group of only the L-isomer of the N-substituted carbonyl compounds such as phosphorus-containing amino acids, glutamic acid, aspartic acid and glutamine to produce corresponding L-amino acids having a high optical purity.

Further, the enzyme is found to be stable enough at a high temperature to retain a high activity of eliminating the substituted carbonyl groups even in the reaction at a temperature of as high as 50° C.

The present invention will be further illustrated with reference to the following examples which is not intended to limit the scope of the invention.

EXAMPLES

Referential Example Synthesis of N-acetyl-D,L-2-amino-4-hydroxy(methyl)phosphinyl-butyric acid D,L-2-amino-4-hydroxy(methyl)phosphinylbutyric acid (4 g, 0.022 mol) was dissolved into 160 g of a mixed solution of water and acetic acid (1 : 1 by weight), followed by addition of 320 g of acetic anhydride under stirring.

Two hours later, the reaction temperature rose to 80° C. owing to the exothermic reaction. So, the reaction mixture was cooled to 20° C. by means of a water-ice bath. After cooling, the mixture was further stirred at 20° C. for 2 hours.

The reaction mixture was concentrated under reduced pressure. Then the residue was analyzed by high performance liquid chromatography, which indicated 100% conversion of D,L-2-amino-4-hydroxy(methyl)-phosphinylbutyric acid into corresponding N-acetylated compound.

When the residue was methylated with diazomethane and subjected to a gas chromatography-mass spectrometric analysis, the methylated product was identified as methyl N-acetyl-D,L-2-amino-4-hydroxy(methyl)-phosphinylbutyrate, 100% yield.

Example 1

One loopful of *Serratia marcescens* IFO 12648 collected from its slant culture was inoculated into 100 ml of a sterile medium containing 1% peptone, 0.5% yeast extract and 0.5% sodium chloride in a 500 ml Erlenmeyer flask and cultivated on a rotary shaker at 150 rpm at 28° C. for 72 hours.

After 48 hours from the beginning of the cultivation, 0.1 g of N-acetyl-D,L-2-amino-4-hydroxy(methyl)phosphinyl-butyric acid was added to induce enzyme production, and the cultivation was further continued for 24 hours.

The resulting liquid culture (i.e., fermentation broth) was centrifuged at 8000 rpm for 20 minutes to obtain the cells. 500 mg of the collected cells and 100 mg of N-acetyl-D,L-2-amino-4-hydroxy(methyl)phosphinyl-butyric acid adjusted to pH 8.0 with conc. ammonia were suspended in 10 ml of a 0.1M tris-hydrochloric acid buffer solution (pH 8.0).

The resulting suspension was added into a 100 ml Erlenmeyer flask and reacted at 28° C for 96 hours on a rotary shaker at 100 rpm.

After the reaction was completed, the mixture was centrifuged to remove the cells, and the supernatant was analyzed by using the optical isomer-separating columns (MCI GEL, manufactured by Mitsubishi Chemical Industries Ltd., and CHIRALPAK WH, manufactured by Daicel Chemical Industries, Ltd.).

The analyzing conditions of the product are as follows:

Column: MCI GEL CRS10W (DLAA), 4.6 mm × 50 mm mfd. by Mitsubishi Chemical Industries Ltd.
Eluent: 2.0mM $CuSO_4$
Flow rate: 1 ml/minute
Temperature: 30° C.

detected at UV wavelength of 254 nm

The analyzing conditions of the unreacted substrate (remaining substrate) are as follows:

Column: CHIRALPAK WH, 4.6 mm × 250 mm mfd. by Daicel Chemical Industries, Ltd.
Eluent: 0.25mM CuSO$_4$
Flow rate: 1.5 ml/minute
Temperature: 30° C.
detected at UV wavelength of 220 nm The result of the analyses indicated the reaction product was L-2-amino-4-hydroxy(methyl)phosphinylbutyric acid.

The conversion of N-acetyl-L-2-amino-4-hydroxy-(methyl)phosphinylbutyric acid into L-2-amino-4-hydroxy-(methyl)phosphinylbutyric acid was 20% and the L-isomer selectivity in the deacetylation (asymmetric hydrolysis) of N-acetyl-D,L-2-amino-4-hydroxy(-methyl)phosphinylbutyric acid was 100%.

EXAMPLE 2

One loopful of *Staphylococcus aureus* IFO 12732 collected from its slant culture was inoculated into 100 ml of a sterile medium containing 1% peptone, 0.5% yeast extract and 0.5% sodium chloride in a 500 ml Erlenmeyer flask and cultivated on a rotary shaker at 150 rpm at 28° C. for 72 hours.

After 48 hours from the beginning of the cultivation, 0.1 g of sodium N-acetyl-L-glutamate was added to induce enzyme production, and the cultivation was further continued for 24 hours. The resulting liquid culture was centrifuged at 8000 rpm for 20 minutes to obtain the cells.

500 mg of the collected cells and 100 mg of N-acetyl-D,L-2-amino-4-hydroxy(methyl)phosphinylbutyric acid adjusted to pH 8.0 with conc. ammonia were suspended in 10 ml of a 0.1M tris-hydrochloric acid buffer solution (pH 8.0). The resulting suspension was added into a 100 ml Erlenmeyer flask and reacted at 28° C for 48 hours on a rotary shaker at 100 rpm.

After the reaction was completed, the mixture was centrifuged to remove the cells, and the supernatant was analyzed under the same conditions as in Example 1 by using the optical isomer-separating columns (MCI GEL, manufactured by Mitsubishi Chemical Industries Ltd., and CHIRALPAK WH, manufactured by Daicel Chemical Industries, Ltd.). From the analyses, the reaction product was determined to be L-2-amino-4-hydroxy(methyl)phosphinylbutyric acid.

The conversion of N-acetyl-L-2-amino-4-hydroxy-(methyl)phosphinylbutyric acid into L-2-amino-4-hydroxy-(methyl)phosphinylbutyric acid was 18% and the L-isomer selectivity in the deacetylation (asymmetric hydrolysis) of N-acetyl-D,L-2-amino-4-hydroxy(-methyl)phosphinylbutyric acid was 100%.

EXAMPLE 3

One loopful of *Actinoplanes liguriae* IFO 13997 collected from its slant culture was inoculated into 100 ml of a sterile medium containing 0.2% yeast extract, 0.2% meat extract, 0.4% polypeptone and 1.0% glucose in a 500 ml Erlenmeyer flask and cultivated on a rotary shaker at 150 rpm at 28° C. for 136 hours.

After 40 hours from the beginning of the cultivation, 0.1 g of sodium N-acetyl-L-glutamate was added to induce enzyme production, and the cultivation was further continued for 40 hours. The resulting liquid culture was centrifuged at 8000 rpm for 20 minutes to obtain the cells.

400 mg of the collected cells and 50 mg of N-acetyl-D,L-2-amino-4-hydroxy(methyl)phosphinylbutyric acid adjusted to pH 8.0 with conc. ammonia were suspended in 5 ml of a 0.1M tris-hydrochloric acid buffer solution (pH 8.0). The resulting suspension was added into a 100 ml Erlenmeyer flask and reacted at 28° C. for 48 hours on a rotary shaker at 100 rpm.

After the reaction was completed, the mixture was centrifuged to remove the cells, and the supernatant was analyzed under the same conditions as in Example 1 by using the optical isomer-separating columns (MCI GEL, manufactured by Mitsubishi Chemical Industries Ltd., and CHIRALPAK WH, manufactured by Daicel Chemical Industries, Ltd.). From the analyses, the reaction product was determined to be L-2-amino-4-hydroxy(methyl)phosphinylbutyric acid.

The conversion of N-acetyl-L-2-amino-4-hydroxy-(methyl)phosphinylbutyric acid into L-2-amino-4-hydroxy-(methyl)phosphinylbutyric acid was 15% and the L-isomer selectivity in the deacetylation (hydrolysis) of N-acetyl-D,L-2-amino-4-hydroxy(methyl)phosphinylbutyric acid was 80%.

EXAMPLE 4

One loopful of *Bacillus brevis* NCB 11 collected from its slant culture was inoculated into 100 ml of a sterile medium containing 1% peptone, 0.5% yeast extract and 0.5% sodium chloride in a 500 ml Erlenmeyer flask and cultivated on a rotary shaker at 150 rpm at 37° C. for 72 hours.

The resulting liquid culture was centrifuged at 8000 rpm for 20 minutes to obtain the cells. 500 mg of the collected cells and 100 mg of N-acetyl-D,L-2-amino-4-hydroxy-(methyl)phosphinylbutyric acid adjusted to pH 8.0 with conc. ammonia were suspended in 10 ml of a 0.1M tris-hydrochloric acid buffer solution (pH 8.0). The resulting suspension was added into a 100 ml Erlenmeyer flask and reacted at 28° C. for 96 hours on a rotary shaker at 100 rpm.

After the reaction was completed, the mixture was centrifuged to remove the cells, and the supernatant was analyzed under the same conditions as in Example 1 by using the optical isomer-separating columns (MCI GEL, manufactured by Mitsubishi Chemical Industries Ltd., and CHIRALPAK WH, manufactured by Daicel Chemical Industries, Ltd.). From the analyses, the reaction product was determined to be L-2-amino-4-hydroxy(methyl)phosphinylbutyric acid.

The conversion of N-acetyl-L-2-amino-4-hydroxy-(methyl)phosphinylbutyric acid into L-2-amino-4-hydroxy-(methyl)phosphinylbutyric acid was 35% and the L-isomer selectivity in the deacetylation (asymmetric hydrolysis) of N-acetyl-D,L-2-amino-4-hydroxy(-methyl)phosphinylbutyric acid was 100%.

EXAMPLE 5

One loopful of Flavobacterium sp. NCB 12-2 collected from its slant culture was inoculated into 100 ml of a sterile medium containing 1% peptone, 0.5% yeast extract and 0.5% sodium chloride in a 500 ml Erlenmeyer flask and cultivated on a rotary shaker at 150 rpm at 30° C. for 72 hours.

The resulting liquid culture was centrifuged at 8000 rpm for 20 minutes to obtain the cells. 500 mg of the collected cells and 100 mg of N-acetyl-D,L-2-amino-4-hydroxy-(methyl)phosphinylbutyric acid adjusted to pH 8.0 with conc. ammonia were suspended in 10 ml of a 0.1M tris-hydrochloric acid buffer solution (pH 8.0). The resulting suspension was added into a 100 ml Erlenmeyer flask and reacted at 28° C. for 96 hours on a rotary shaker at 100 rpm.

After the reaction was completed, the mixture was centrifuged to remove the cells, and the supernatant was analyzed under the same conditions as in Example 1 by using the optical isomer-separating columns (MCI GEL, manufactured by Mitsubishi Chemical Industries Ltd., and CHIRALPAK WH, manufactured by Daicel Chemical Industries, Ltd.). From the analyses, the reaction product was determined to be L-2-amino-4-hydroxy(methyl)phosphinylbutyric acid.

The conversion of N-acetyl-L-2-amino-4-hydroxy-(methyl)phosphinylbutyric acid into L-2-amino-4-hydroxy-(methyl)phosphinylbutyric acid was 30% and the L-isomer selectivity in the deacetylation (asymmetric hydrolysis) of N-acetyl-D,L-2-amino-4-hydroxy(methyl)phosphinylbutyric acid was 100%.

EXAMPLE 6

One loopful of Achromobacter sp. IFO 13495 collected from its slant culture was inoculated into 100 ml of a sterile medium containing 0.1% potassium dihydrogenphosphate, 0.1% potassium monohydrogenphosphate, 0.01% magnesium sulfate, 1% glycerol, 1% tryptone, 1% yeast extract and 0.1% N-acetyl-D,L-2-amino-4-hydroxy(methyl)phosphinylbutyric acid (pH 7.0) in a 500 ml Erlenmeyer flask and cultivated on a rotary shaker at 150 rpm at 30° C. for 48 hours.

The resulting liquid culture was centrifuged at 8000 rpm for 20 minutes to obtain the cultured cells. The collected cells (500 mg) was suspended into 10 ml of 0.1M phosphate buffer solution (pH 7.5) containing 100 mg of N-acetyl-D,L-2-amino-4-hydroxy(methyl)phosphinylbutyric acid.

The resulting suspension was added into a 100 ml Erlenmeyer flask and reacted at 30° C. for 48 hours on a rotary shaker at 100 rpm.

After the reaction was completed, the mixture was centrifuged to remove the cells, and the supernatant was analyzed under the same conditions as in Example 1 by using the optical isomer-separating columns (MCI GEL, manufactured by Mitsubishi Chemical Industries Ltd., and CHIRALPAK WH, manufactured by Daicel Chemical Industries, Ltd.). From the analyses, the reaction product was determined to be L-2-amino-4-hydroxy(methyl)phosphinylbutyric acid.

The conversion of N-acetyl-L-2-amino-4-hydroxy-(methyl)phosphinylbutyric acid into L-2-amino-4-hydroxy-(methyl)phosphinylbutyric acid was 25% and the L-isomer selectivity in the deacetylation (asymmetric hydrolysis) of N-acetyl-D,L-2-amino-4-hydroxy(methyl)phosphinylbutyric acid was 100%.

EXAMPLE 7

One loopful of Alcaligenes latus NCB 4-12 collected from its slant culture was inoculated into 100 ml of a sterile medium containing 1% glucose, 1% ammonium chloride, 0.1% potassium dihydrogenphosphate, 0.1% potassium monohydrogenphosphate, 0.025% magnesium sulfate, 0.001% manganese sulfate, 0.001% ferrous sulfate, 0.001% cobalt chloride and 0.05% yeast extract (pH 7.0) in a 500 ml Erlenmeyer flask and cultivated on a rotary shaker at 150 rpm at 30° C. for 72 hours.

The resulting liquid culture was centrifuged at 8000 rpm for 20 minutes to obtain the cells. The collected cells (500 mg) was suspended into 10 ml of 0.1M phosphate buffer solution (pH 7.5) containing 1% N-acetyl-D,L-2-amino-4-hydroxy(methyl)phosphinylbutyric acid.

The resulting suspension was added into a 100 ml Erlenmeyer flask and reacted at 30° C. for 48 hours on a rotary shaker at 100 rpm.

After the reaction was completed, the mixture was centrifuged to remove the cells, and the supernatant was analyzed under the same conditions as in Example 1 by using the optical isomer-separating columns (MCI GEL, manufactured by Mitsubishi Chemical Industries Ltd., and CHIRALPAK WH, manufactured by Daicel Chemical Industries, Ltd.). From the analyses, the reaction product was determined to be L-2-amino-4-hydroxy(methyl)phosphinylbutyric acid.

The conversion of N-acetyl-L-2-amino-4-hydroxy-(methyl)phosphinylbutyric acid into L-2-amino-4-hydroxy-(methyl)phosphinylbutyric acid was 78% and the L-isomer selectivity in the deacetylation (asymmetric hydrolysis) of N-acetyl-D,L-2-amino-4-hydroxy(methyl)phosphinylbutyric acid was 100%.

EXAMPLE 8

One loopful of Sebekia benihana IFO 14309 collected from its slant culture was inoculated into 100 ml of a sterile medium containing 1% maltose, 0.5% polypeptone, 0.05% yeast extract, 0.1% potassium dihydrogenphosphate, 0.1% potassium monohydrogenphosphate, 0.025% magnesium sulfate heptahydrate, 0.001% manganese sulfate tetrahydrate and 0.001% ferrous sulfate heptahydrate (pH 7.0) in a 500 ml Erlenmeyer flask and cultivated on a rotary shaker at 150 rpm at 28° C. for 60 hours.

The resulting liquid culture was centrifuged at 8000 rpm for 15 minutes to obtain the cells. The collected cells (500 mg) was suspended into 10 ml of 0.1M phosphate buffer solution (pH 7.5) containing 1% N-acetyl-D,L-2-amino-4-hydroxy(methyl)phosphinylbutyric acid.

The resulting suspension was added into a 100 ml Erlenmeyer flask and reacted at 28° C. for 48 hours on a rotary shaker at 100 rpm.

After the reaction was completed, the mixture was centrifuged to remove the cells, and the supernatant was analyzed under the same conditions as in Example 1 by using the optical isomer-separating columns (MCI GEL, manufactured by Mitsubishi Chemical Industries Ltd., and CHIRALPAK WH, manufactured by Daicel Chemical Industries, Ltd.). From the analyses, the reaction product was determined to be L-2-amino-4-hydroxy(methyl)phosphinylbutyric acid.

The conversion of N-acetyl-L-2-amino-4-hydroxy-(methyl)phosphinylbutyric acid into L-2-amino-4-hydroxy-(methyl)phosphinylbutyric acid was 23% and the L-isomer selectivity in the deacetylation (asymmetric hydrolysis) of N-acetyl-D,L-2-amino-4-hydroxy(methyl)phosphinylbutyric acid was 100%.

EXAMPLE 9

One loopful of Streptosporangium sp. NC 26 collected from its slant culture was inoculated into 100 ml of a sterile medium containing 1% maltose, 0.5% polypeptone, 0.05% yeast extract, 0.1% potassium dihydrogenphosphate, 0.1% potassium monohydrogenphosphate, 0.025% magnesium sulfate heptahydrate, 0.001% manganese sulfate tetrahydrate and 0.001% ferrous sulfate heptahydrate (pH 7.0) in a 500 ml Erlenmeyer flask and cultivated on a rotary shaker at 150 rpm at 28° C. for 60 hours to prepare a seed culture.

The seed liquid culture thus prepared was inoculated into 500 ml of a medium of the same composition as above in a 5 liter Erlenmeyer flask at a concentration of 1% and cultivated on a rotary shaker at 180 rpm at 28° C. for 60 hours.

The resulting liquid culture was centrifuged at 10000 rpm for 20 minutes to obtain the cells which was then washed with 500 ml of a physiological saline.

From 2 liter of the liquid culture in total, there was obtained 67 g (wet cell weight) of washed cells of Streptosporangium sp. NC 26 strain.

EXAMPLE 10

Into 20 ml of distilled water were suspended 1.5 g of the wet cells obtained in Example 9 and 3 g of N-acetyl-D,L-2-amino-4-hydroxy(methyl)phosphinylbutyric acid adjusted to pH 7.8 with conc. ammonia. The resulting suspension was placed in a 50 ml cylindrical tube and reacted at 40° C. for 48 hours under shaking.

Figure 2:
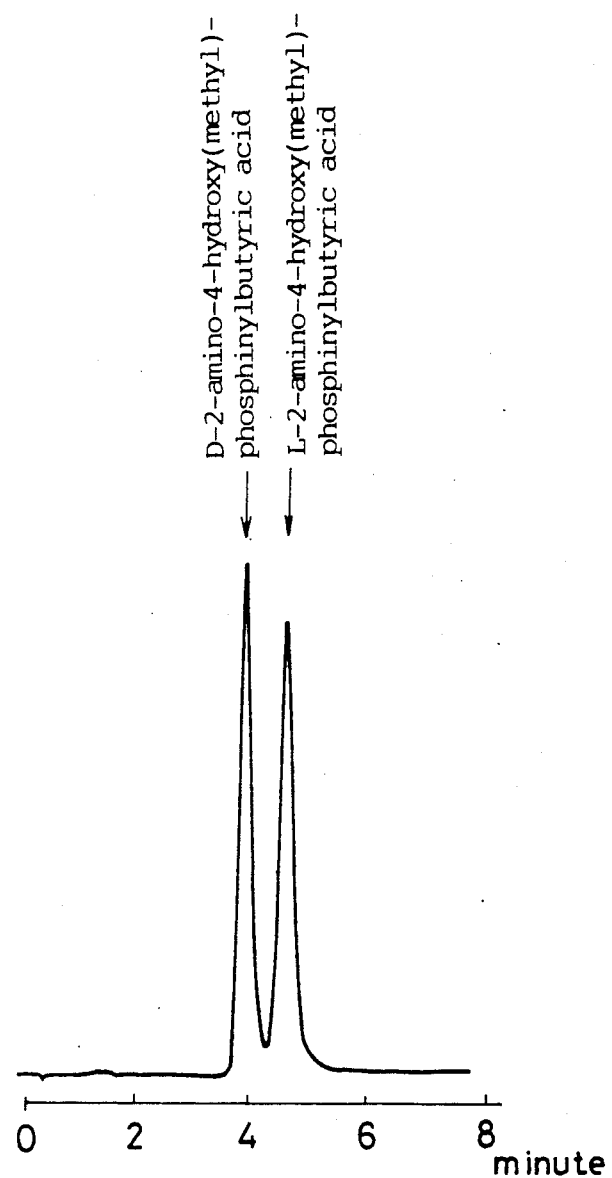
Figure 3:
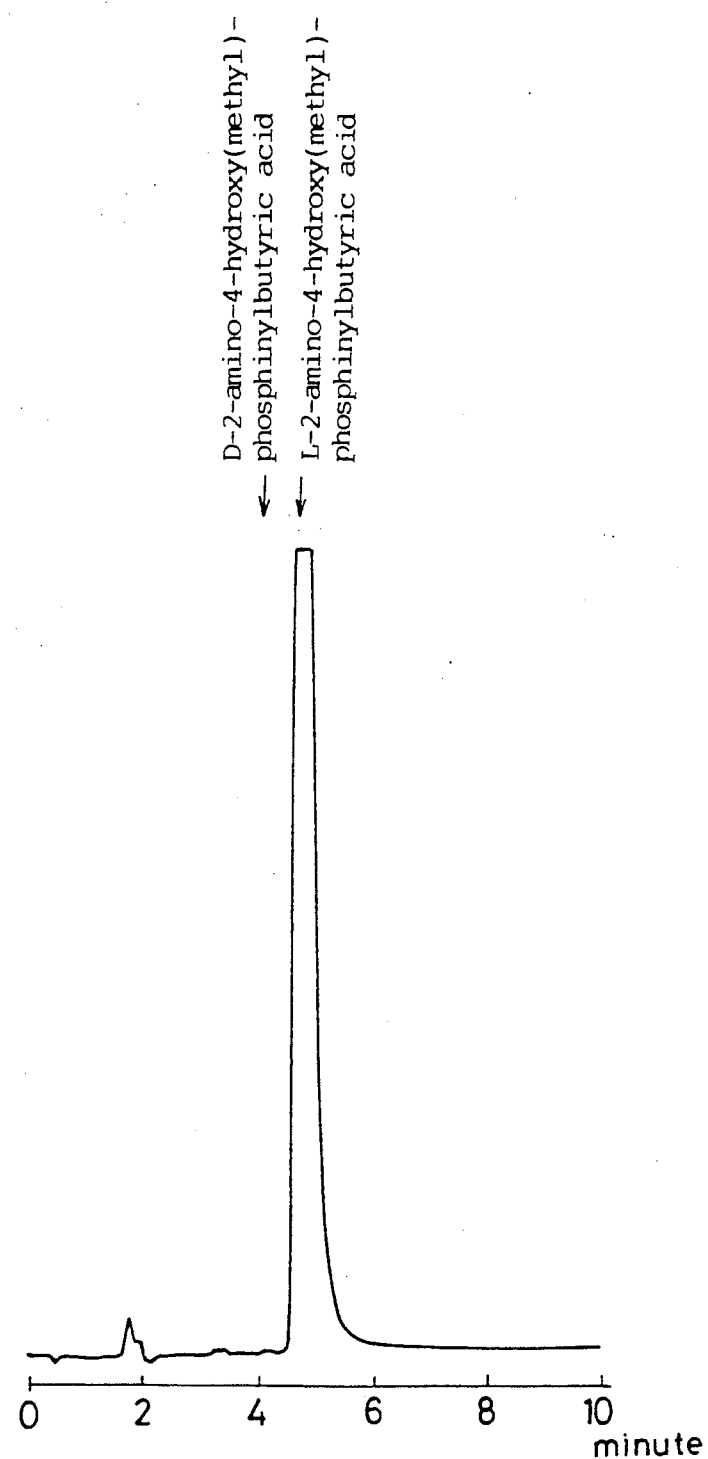

After the reaction was completed, the mixture was centrifuged to remove the cells, and the supernatant was analyzed under the same conditions as in Example 1 by using the optical isomer-separating columns (MCI GEL, manufactured by Mitsubishi Chemical Industries Ltd., and CHIRALPAK WH, manufactured by Daicel Chemical Industries, Ltd.). FIG. 1 shows a chart of the reaction product at high performance liquid chromatography (MCI GEL CRS10W column). FIG. 2 shows a chart of racemic 2-amino-4-hydroxy(methyl)phosphinyl-butyric acid at the analysis. The supernatant was passed through a column of Dowex 50W X8 (H+) and eluted with water. The fractions positive at ninhydrin test were collected and concentrated under reduced pressure followed by the analysis using MCI GEL CRS10W column. The result is shown in FIG. 3. In these charts, peak height is plotted as ordinate and retention time (minute) as abscissa.

As shown in the charts, the reaction product was L-2-amino-4-hydroxy(methyl)phosphinylbutyric acid alone of which optical purity was more than 99.8% e.e., and corresponding D-isomer was hardly detected.

The conversion of N-acetyl-L-2-amino-4-hydroxy-(methyl)phosphinylbutyric acid into L-2-amino-4-hydroxy-(methyl)phosphinylbutyric acid was 100% and the L-isomer selectivity in the deacetylation (asymmetric hydrolysis) of N-acetyl-D,L- 2-amino-4-hydroxy(methyl)phosphinylbutyric acid was 100%.

EXAMPLE 11

Into 5 ml of 100mM phosphate buffer solution (pH 7.5) were suspended 500 mg of the wet cells of Streptosporangium sp. NC 26 obtained in Example 9, and 50 mg of sodium N-acetyl-D,L-2-amino-4-hydroxy(methyl)phosphinylbutyrate was added. The resulting mixture was reacted at 30° C. for 24 hours under shaking.

After the reaction was completed, the mixture was centrifuged at 12000 rpm for 20 minutes to remove the cells. The separated cells were again added to 5 ml of 100mM phosphate buffer solution (pH 7.5) containing 1% sodium N-acetyl-D,L-2-amino-4-hydroxy(methyl)-phosphinylbutyrate and the whole was reacted in the same manner as above.

This reaction was repeated three times in total using the same cells. The obtained supernatants were analyzed by using the optical isomer-separating column (MCI GEL, manufactured by Mitsubishi Chemical Industries Ltd.) to determine the conversion (%) of N-acetyl-L-2-amino-4-hydroxy-(methyl)phosphinylbutyric acid into L-2-amino-4-hydroxy-(methyl)phosphinylbutyric acid and the L-isomer selectivity (%) in the deacetylation (asymmetric hydrolysis) of N-acetyl-D,L-2-amino-4-hydroxy(methyl)phosphinylbutyric acid.

The results are as follows:

|  | Conversion (%) | Selectivity (%) |
| --- | --- | --- |
| First time | 100 | 100 |
| Second time | 100 | 100 |
| Third time | 97 | 100 |

EXAMPLE 12

To 1 g of cultivated and washed wet cells of Streptosporangium sp. NC 26 obtained in Example 9 was added 5 ml of 3% kappa-carragheenan which had been heated and dissolved at 60° C. in advance, and the whole was thoroughly mixed.

The mixed solution was cooled and solidified upon gelation by adding a 2% potassium chloride solution.

The solidified product was cut into pieces of 5 mm square, and these square pieces were washed to obtain immobilized cells. The following experiments were carried out by using the immobilized cells thus prepared.

The immobilized cells corresponding to 500 mg of wet cells were added to 10 ml of an aqueous solution containing 2.5% N-acetyl-D,L-2-amino-4-hydroxy(methyl)phosphinylbutyric acid adjusted to pH 7.5 with a sodium hydroxide solution, and the whole was reacted at 30° C. or 40° C. for 24 hours.

The reaction mixture was centrifuged to separate the immobilized cells, and the latter were again added to 10 ml of an aqueous solution containing 2.5% sodium N-acetyl-D,L-2-amino-4-hydroxy(methyl)phosphinylbutyrate (pH 7.5), and the whole was reacted in the same manner as above.

The resulting L-2-amino-4-hydroxy(methyl)phosphinyl-butyric acid was subjected to the same quantitative analysis as in Example 1. The decrease of the enzyme activity in the immobilized cells after repeating the reaction seven times was 7% in the reaction at 30° C., and 8% at 40° C.

EXAMPLE 13

The above reaction was repeated using the cells of Streptosporangium sp. NC 26 at different reaction temperatures, i.e., 25° C., 30° C., 40° C. and 50° C, and the amounts of L-2-amino-4-hydroxy(methyl)phosphinyl-butyric acid produced from N-acetyl-D,L-2-amino-4-hydroxy(methyl)-phosphinylbutyric acid were determined by high performance liquid chromatography.

The amounts of L-2-amino-4-hydroxy(methyl)phosphinyl-butyric acid produced after 24 hour-reaction at the respective temperature by adding 20 mg of wet cells to 1 ml of 5% N-acetyl-D,L-2-amino-4-hydroxy(methyl)phosphinyl-butyric acid (pH 7.0) are shown in the following.

| Reaction temperature (°C.) | 25 | 30 | 40 | 50 |
| --- | --- | --- | --- | --- |
| Amount produced (mg/ml) | 6.1 | 7.6 | 12.4 | 10.0 |

EXAMPLE 14

Production of corresponding L-amino acids from N-acetyl-D,L-amino acids was examined by using *Alcaligenes latus* NCB 4-12 or *Streptosporangium* sp. NC 26. The results are shown in the following table.

The "relative activity" in the table indicates the values relative to the amount (mg/ml) of the produced L-2-amino-4-hydroxy(methyl)phosphinylbutyric acid which is given as 100.

| Substrate | Relative activity | |
|---|---|---|
| | NCB 4-12 | NC 26 |
| N-acetyl-D,L-2-amino-4-hydroxy (methyl)phosphinylbutyric acid | 100 | 100 |
| N-acetyl-D,L-glutamic acid | 124 | 115 |
| N-acetylglycine | 89 | 27 |
| N-acetyl-D,L-methionine | 26 | 29 |
| N-acetyl-D,L-leucine | 140 | 187 |
| N-acetyl-D,L-glutamine | 150 | 385 |
| N-acetyl-D,L-aspartic acid | 46 | 40 |

EXAMPLE 15

Into 2 ml of distilled water was suspended well 100 ml of washed cells of Streptosporangium sp. NC 26 prepared in the same manner as in Example 9. After adding 20 mg of sodium N-acetyl-D,L-2-amino-4-ethoxy(methyl)phosphinyl-butyrate, the whole was reacted at 30° C. for 48 hours under shaking.

The reaction mixture was centrifuged at 12000 rpm for 20 minutes to separate the cells.

The supernatant was analyzed under the same conditions as in Example 1 by using the optical isomer-separating columns (MCI GEL, manufactured by Mitsubishi Chemical Industries Ltd., and CHIRALPAK WH, manufactured by Daicel Chemical Industries, Ltd.). From the analyses, the reaction product was identified as L-2-amino-ethoxy(methyl)phosphinyl-butyric acid.

When the above reaction was conducted by using 20 mg of sodium N-acetyl-D,L-2-amino-4-[(2-chloroethoxy)methyl-phosphinyl]butyrate as a substrate, the product was determined to be L-2-amino-4-[(2-chloroethoxy)methyl-phosphinyl]butyric acid upon the above chromatographic analyses.

The products, L-2-amino-4-ethoxy(methyl)phosphinyl-butyric acid and L-2-amino-4-[(2-chloroethoxy)-methyl-phosphinyl]butyric acid could be easily hydrolyzed at their ester portion by the action of a commercially available esterase (e.g., acetylcholinesterase) or by chemical hydrolysis reaction to give L-2-amino-4-hydroxy(methyl)-phosphinylbutyric acid.

What is claimed is:

1. A process for producing an L-amino acid represented by the formula (I):

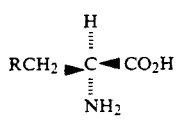  (I)

wherein R is —CH$_2$CO$_2$H, —CH$_2$CONH$_2$, —CO$_2$H or

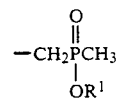

in which R$^1$ is hydrogen atom, an alkyl group having 1 to 10 carbon atoms or a halogen-substituted alkyl group having 1 to 10 carbon atoms,
which process comprises optically resolving an N-substituted carbonyl-D,L-amino acid represented by the formula (II);

  (II)

wherein R is as defined above and R$^2$ is an alkanoyl group having 1 to 5 carbon atoms, a benzoyl group, a halogen-substituted alkanoyl group having 1 to 5 carbon atoms or a halogen-substituted benzoyl group, its salt or a mixture thereof,
by a microorganism, a fermentation broth obtained by cultivating the microorganism, or a mixture thereof, said microorganism being a bacterial strain selected from the group consisting of *Serratia mercascens* IFO 12648, *Staphlococcus aureus* IFO 12732, *Bacillus brevis* NCB 11 (FERM BP-2551), *Flavobacterium sp.* NCB 12-2 (FERM BP-2552), *Achromobacter sp.* IFO 13495, *Alcaligenes latus* NCB 4-12 (FERM BP-2553), *Actinoplanes liguriae* IFO 13997, *Streptosporangium sp.* NC 26 (FERM BP-2554), and *Sebekia benihana* IFO 14309.

2. The process according to claim 1 wherein the strain is *Staphlococcus aureus* IFO 12732.

3. The process according to claim 1 wherein the strain is *Bacillus brevis* NCB 11 (FERM BP-2551).

4. The process according to claim 1 wherein the strain is *Flavobacterium sp.* NCB 12-2 (FERM BP-2552)

5. The process according to claim 1 wherein the strain is Achromobacter sp. IFO 13495.

6. The process according to claim 1 wherein the strain is *Alcaligenes latus* NCB 4-12 (FERM BP-2553).

7. The process according to claim 1 wherein the strain is *Actinoplanes liguriae* IFO 13997.

8. The process according to claim 1 wherein the strain is Streptosporangium sp. NC 26 (FERM BP-2554).

9. The process according to claim 1 wherein the strain is Sebekia benihana IFO 14309.

10. The process according to claim 1, wherein the substituted carbonyl group R$^2$ is acetyl group.

11. The process according to claim 1, wherein the optical resolution is carried out at a temperature of 10 to 60° C.

12. The process according to claim 11 wherein the optical resolution is carried out at a temperature of 20° to 50° C.

13. The process according to claim 1, wherein the optical resolution is carried out at a pH of 4 to 10.

14. The process according to claim 13, wherein the optical resolution is carried out at a pH of 6 to 9.

* * * * *